United States Patent [19]
Aslund et al.

[11] Patent Number: 5,418,371
[45] Date of Patent: *May 23, 1995

[54] APPARATUS FOR QUANTITATIVE IMAGING OF MULTIPLE FLUOROPHORES USING DUAL DETECTORS

[76] Inventors: Nils R. D. Aslund, Skontorpsvagen 126, 9 tr, S-121 65 Johanneshov, Stockholm; Kjell S. Carlsson, Malmbodavagen 17, S-186 42 Vallentuna, both of Sweden

[*] Notice: The portion of the term of this patent subsequent to Mar. 15, 2011 has been disclaimed.

[21] Appl. No.: 189,190

[22] Filed: Jan. 31, 1994

Related U.S. Application Data

[63] Continuation-in-part of Ser. No. 11,881, Feb. 1, 1993, Pat. No. 5,294,799.

[51] Int. Cl.$^6$ .............................. G01N 21/64
[52] U.S. Cl. .................. 250/458.1; 250/459.1
[58] Field of Search ........... 250/458.1, 459.1, 461.1, 250/462.2; 356/317, 318

[56] References Cited

U.S. PATENT DOCUMENTS

| | | | |
|---|---|---|---|
| 4,628,026 | 12/1986 | Gardell et al. | 435/7 |
| 4,937,457 | 6/1990 | Mitchell | 250/458.1 |
| 5,208,651 | 5/1993 | Buican | 356/346 |
| 5,212,386 | 5/1993 | Gratton et al. | 250/458.1 |
| 5,294,799 | 3/1994 | Aslund et al. | 250/458.1 |

FOREIGN PATENT DOCUMENTS

92/13265 of 0000 WIPO .................... 21/64

OTHER PUBLICATIONS

Wessendorf et al., "Multicolor Fluorescence microscopy Using the Laser-Scanning Confocal Microscope", *Neuroprotocols: A Companion to Methods in Neurosciences 2*, pp. 121–140 (1993).

Ira Kurtz, "Apical Na+/H+ Antiporter and Glycolysis-dependent H+-ATPase Regulate Intracellular pH in the Rabbit S3 Proximal Tubule", *J. Clin. Invest.*, vol. 80, pp. 928–935 (Oct., 1987).

Carlsson et al., "Reduction of cross-talk between fluorescent Labels in scanning laser microscopy", *Journal of Microscopy*, vol. 167, Pt. 1, pp.23–37 (Jul., 1992).

Wang et al., "H+/base transport in principal cells characterized by confocal fluorescence imaging", *Am. J. Physiol. 259 (Cell Physiol. 28)*, pp. C365–C373 (1990).

Joseph R. Lakowicz, et al., "Frequency-domain fluorescence spectroscopy, a new method for the resolution of complex fluoresnce emission," *Trends in Analytical Chemistry*, vol. 5, No. 10, Dec. 1986, pp. 257–263.

Joseph R. Lakowicz, "Fluorescence lifetime sensing," *Laser Focus World*, vol. 28, No. 5, May 1992, pp. 60–80.

C. G. Morgan, et al., "Fluorescence decay time imaging using an Imging Photon Detector with a radiofrequency photon correlation system," *Proceedings SPIE: Time-Resolved Laser Spectroscopy in Biochemistry II*, vol. 1204, Jan. 1990, pp. 798–807.

Primary Examiner—Paul M. Dzierzynski
Assistant Examiner—Richard Henig
Attorney, Agent, or Firm—Schneck & McHugh

[57] ABSTRACT

A quantitative fluorometer for multiple fluorophores having dual time-modulated beams of excitation light. Each beam is synchronized with a separate detector and lock-in amplifier. The fluorophores are simultaneously excited and the combined fluorescent emission is resolved into components corresponding to each fluorophore. Confocal scanning means are used to excite and detect fluorescent emission from locations throughout a volume. The location specific output of each amplifier is stored in a computer which resolves the emission into the components corresponding to each fluorophore. The location specific data may be further processed or visually displayed. Multiple amplifiers for each detector channel allow phase discrimination in each channel so that prompt and delayed fluorescence may be measured, allowing use of multiple fluorophores in each detector channel.

21 Claims, 4 Drawing Sheets

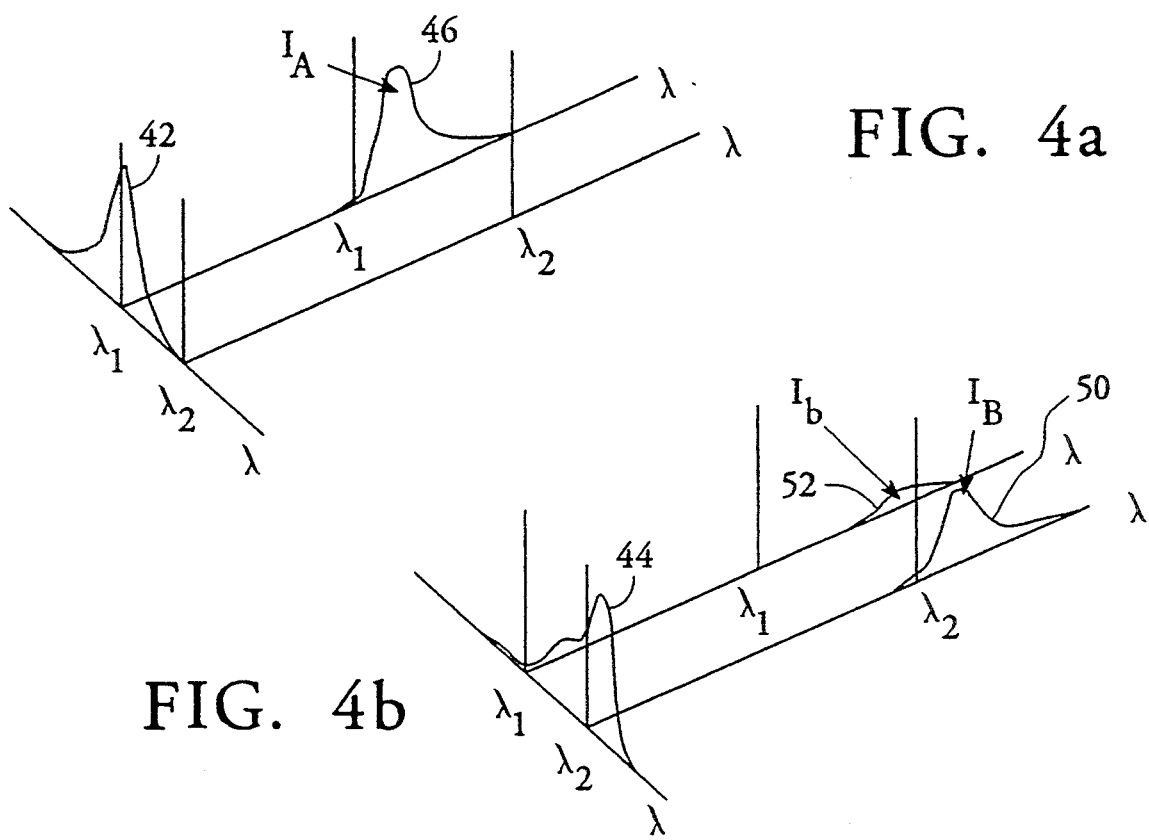
FIG. 4a
FIG. 4b
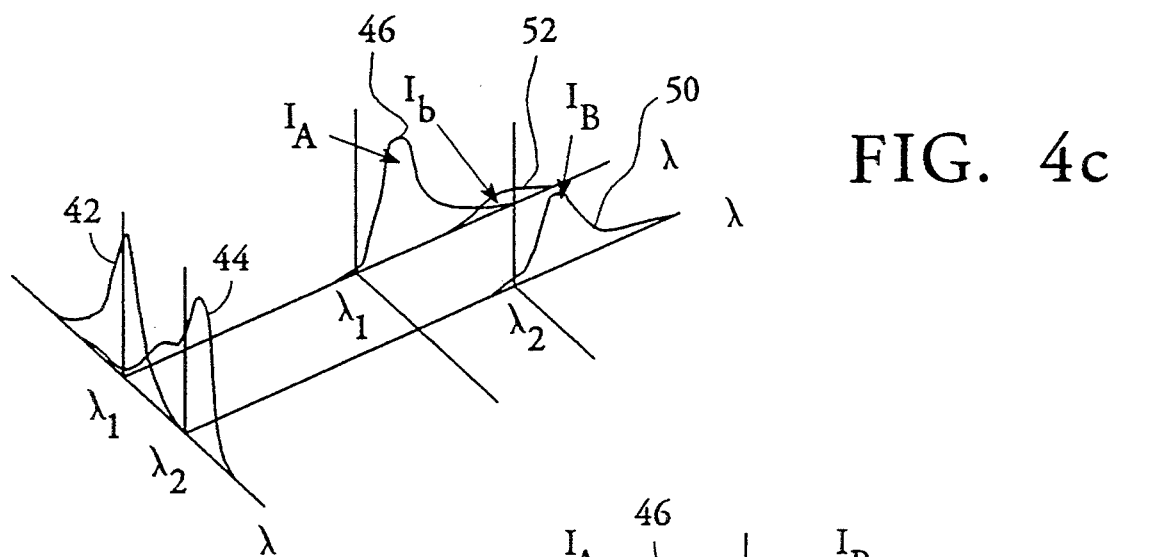
FIG. 4c
FIG. 4d

APPARATUS FOR QUANTITATIVE IMAGING OF MULTIPLE FLUOROPHORES USING DUAL DETECTORS

This application is a continuation-in-part of prior application Ser. No. 08/011,881, filed Feb. 1, 1993.

FIELD OF THE INVENTION

This invention relates to quantitative microfluorometry and more particularly to a device for quantitative microfluorometry in which fluorophores are quantified by simultaneous excitation at two or more wavelengths.

BACKGROUND ART

Recent development of fluorescent indicator dyes for biologically important intracellular components has made it possible to follow the time-dependent distribution of these components in intact cells. For example, see U.S. Pat. Nos. 5,049,673, 4,849,362 and 4,603,208.

The emitted fluorescent radiation from a fluorophore in response to excitation of a single wavelength generally includes a broad band of wavelengths. Spectra of emissions from different fluorophores will generally overlap. Also, when using radiations of different wavelengths to excite each of two fluorophores, their emission spectra may still overlap.

Fluorophores absorb excitation radiation at more than one wavelength. The absorption spectra of different fluorophores may overlap. As a consequence, radiation of a wavelength chosen to efficiently excite a certain fluorophore will also to some extent excite other fluorophores. There may occur spectral overlappings between these cross-excited emission spectra of other fluorophores and the emission spectrum of the fluorophore predominantly excited by the chosen wavelength. In summary, in many applications involving multiple fluorophores the fact that their emission spectra generally overlap and that their absorption spectra also may overlap constitutes a major problem. Making simultaneous quantitative measurements of the individual fluorophores is difficult or impossible. Therefore, in the past, simultaneous fluorescent detection has been primarily limited to cases where the wavelength regions of spectral overlap of the emissions can be suppressed by optical filtering. Then separation is achieved at the expense of losing valuable signal intensity.

The different emission spectra of a single fluorophore obtained by exciting it with different wavelengths generally overlap heavily and can not be separated by optical filtering. The relative intensities of these spectra depend on the shape of the absorption spectrum. This shape may convey valuable information about the fluorophore and its environment. Thus, there is a need to separately measure the cross-excited emission of a fluorophore and the main emission, thereby collecting information about the shape of the absorption spectrum. To achieve this in the case when two different fluorophores are present and two excitation wavelengths are simultaneously applied, the individual contributions from each fluorophore must be measured separately. This can not be done by optical filtering exclusively.

When a fluorophore is excited by light having a sinusoidally modulated intensity, the fluorescence emitted is also sinusoidally modulated. The modulation frequencies are the same but the phase of the emitted fluorescence is shifted by an amount related to the lifetime of the fluorophore's excited state. Mitchell U.S. Pat. No. 4,937,457 discloses a frequency domain spectrofluorometer which uses a single wavelength of excitation modulated at multiple harmonically related phase-locked frequencies to simultaneously determine the spectral response and phase shift of a single fluorophore to the entire range of modulation frequencies employed. The data produced is used to determine the fluorescence lifetime of a fluorophore.

In Takahashi U.S. Pat. No. 5,032,714 et al., a light waveform measuring device is used for measuring the lifetime of fluorescent light produced due to pulsed laser excitation. Two laser beams of different frequencies, at least one of which is pulsed, are used to produce a single-frequency pulsed beam selected from the sum frequency mixing of the beams. The output beam is pulsed at the same rate as the pulsed input beam which is used to trigger a single-photon detector or streak camera. The detector is thereby synchronized to the exciting beam.

Identification and discrimination of multiple fluorophores in a sample is disclosed in Loken U.S. Pat. No. 5,047,321 et al. Each component must have a distinguishable characteristic peak emission wavelength at which a detector is set. Fluorophores may be excited with a single wavelength or multiple wavelengths, but detection occurs in regions where the peak emission spectra do not overlap.

In Gardell U.S. Pat. No. 4,628,026 et al., an automated system for the sequential and alternate irradiation of a specimen by two distinguishable wavelengths of light is disclosed. The system classifies specimens based on the quotient of the fluorescent light intensities sequentially received from the specimen in response to the two excitation wavelengths.

Simultaneous recording of multiple fluorophores excited by a single wavelength using spectral filtering or separation is disclosed in Robertson, Jr. U.S. Pat. No. 4,833,332 to et al. The fluorophores which have overlapping emission spectra are distinguished by the ratio of their emissions transmitted by two spectral filters having complementary transmission spectra. The system is not capable of quantitative determinations.

The prior art devices which measure fluorescence at only one peak emission wavelength are unable to simultaneously quantify multiple fluorophores using the total emission from each fluorophore. Those devices which rely on spectral separation to distinguish multiple fluorophores are unable to separate the total contribution of each fluorophore from the combined emission spectrum detected.

Use of lock-in amplifiers for signal detection is known. Using a two-phase, rather than a single-phase lock-in amplifier, the value of the phase angle can be derived from the outputs of the in-phase and the quadrature channels of the amplifier. This has been used, for example, in cytometry by Steinkamp and Crissman (1992) to distinguish between fluorophores that have different decay times. It has also been proposed by Morgan et al. (1992) that this technique should be used in a confocal scanning microscope to produce images that represent the decay time measured at each picture point. A non-confocal system that records the decay times in all picture elements simultaneously has been implemented by Lakowicz and Berndt (1991). In a system reported by Kurtz (1987) for studying objects in a continually flowing solution, a single fluorophore is excited using two modulated excitation wavelengths. Two lock-in amplifiers are used in the system, which performs measurements at a single point and produces no images.

Another method to distinguish between fluorophores with different decay times is to use a repetitive source of short optical pulses and employ time-correlated single-photon counting. This technique has also been combined with imaging. A non-confocal system of this kind has been implemented by Morgan and Murray (1991). A confocal system using time gating has been implemented by Buurman et al. (1992).

The term fluorescence lifetime imaging (FLIM) is used for techniques that represent a combination of decay time measurements and imaging, see Lakowicz and Berndt, (1991).

It is an object to provide an improved microfluorometer capable of simultaneously quantifying multiple fluorophores with greater efficiency.

It is another object of the present invention to provide an improved microfluorometer which simultaneously utilizes the entire emissions of multiple fluorophores or the entire emission spectra except possibly for minor parts.

It is a further object to provide an improved microfluorometer capable of separating the individual contributions from fluorophores having overlapping absorption spectra from the combined emission spectrum detected.

SUMMARY OF THE INVENTION

The above objects have been achieved in a microfluorometer which simultaneously excites a plurality of fluorescent targets at a single location with two or more wavelengths. In the preferred embodiment, each excitation wavelength is chosen to predominantly excite one of the fluorophores. The radiation emitted in response to this combined excitation is separated into spectral parts representing different wavelength bands. Optical filtering and optical beam splitting is employed to achieve this separation. Dual detectors are used to detect the separated spectral parts of the combined emission.

The intensity of the excitation at each wavelength is time-modulated at a separate frequency. A frequency-locked amplifier synchronized to a corresponding modulation frequency is attached to each detector. The discrimination performed by the frequency-locked amplifiers, in combination with the separation into spectral parts performed by optical filters and a beam splitter allows extraction and measuring of contributions representing each separate fluorophore exclusively. This is achieved despite that the emission spectra of the fluorophores may overlap heavily and despite the possible presence of cross-excited spectra, which arise when the wavelength that predominantly excites a certain fluorophore also to some extent excites another fluorophore.

In another preferred embodiment, two single-phase lock-in amplifiers are attached to each detector. The two amplifiers are synchronized with different frequencies, viz. the frequencies used to modulate the intensity of the excitation at each of two excitation wavelengths. All the individual components of the composed emission, including cross-excited contributions, are extracted and measured.

In still another embodiment using two single-phase amplifiers attached to each detector, the two amplifiers are tuned to the same frequency. The two amplifiers attached to the one detector are both tuned to the frequency used to modulate the intensity of the excitation at the one excitation wavelength; the two amplifiers attached to the other detector are both tuned to the frequency used to modulate the intensity of the excitation at the other excitation wavelength. The phase positions of the two amplifiers attached to each detector are 90° apart. Together the two amplifiers perform the function of a dual-phase lock-in amplifier encompassing an in-line and a quadrature channel. The described embodiment is thus identical to an embodiment where a dual-phase lock-in amplifier is attached to each detector.

The two outputs from each dual-phase amplifier are processed to obtain the magnitude and the phase angle of the signal applied to the amplifier, employing well-known techniques. Preferably this is performed digitally, by a data processing unit attached to the outputs. As a result the amplitude of the modulated signal received by the detector, and a phase angle, are derived.

The phase angle represents, in a relative scale, the shift between the phase angle of the modulated excitation and the phase angle of the detected emission. If the molecular relaxation time of a fluorophore changes, as it may do, e.g., due to a change of the pH value of the environment of the fluorophore, this phase shift will change. The effect is substantial if the modulation frequency is high. Therefore, in the present embodiment, the modulation frequency used is preferably an order of magnitude higher than in the previously described embodiments. The device, according to the described embodiment supplies, simultaneously and independently, the phase shifts for two different fluorophores.

In all embodiments, confocal scanning optics may be used for pixel-by-pixel scanning of a stack of planes, so that volumetric data may be obtained, simultaneously and independently, from different fluorophores. Data may be stored in a computer and later displayed. Different colors may be used to distinguish regions representing different intensities of a fluorophore or, in one of the embodiments, different decay times of a fluorophore. In the latter case, a FLIM image is obtained. Alternatively, colors may be used to distinguish contributions from different fluorophores. A three-dimensional image of the volume may be re-created and closely inspected using image-processing techniques, such as generating projections from different angles, zooming etc.

An advantage of the microfluorometer is that multiple fluorophores are simultaneously and independently quantified with greater efficiency.

Another advantage is that contributions from different fluorophores are measured with negligible loss of information, despite their emission spectra overlap and despite interference from cross-excited spectra.

Another advantage is that all the contributions from each fluorophore, including cross-excited spectra, may be simultaneously measured.

A further advantage is that fluorescent lifetime images from different fluorophores are simultaneously recorded.

BRIEF DESCRIPTION OF THE DRAWINGS

FIGS. 4a-d are plots showing the individual spectral components of a combined emission spectrum.

DETAILED DESCRIPTION OF THE PREFERRED EMBODIMENTS

Figure 1:
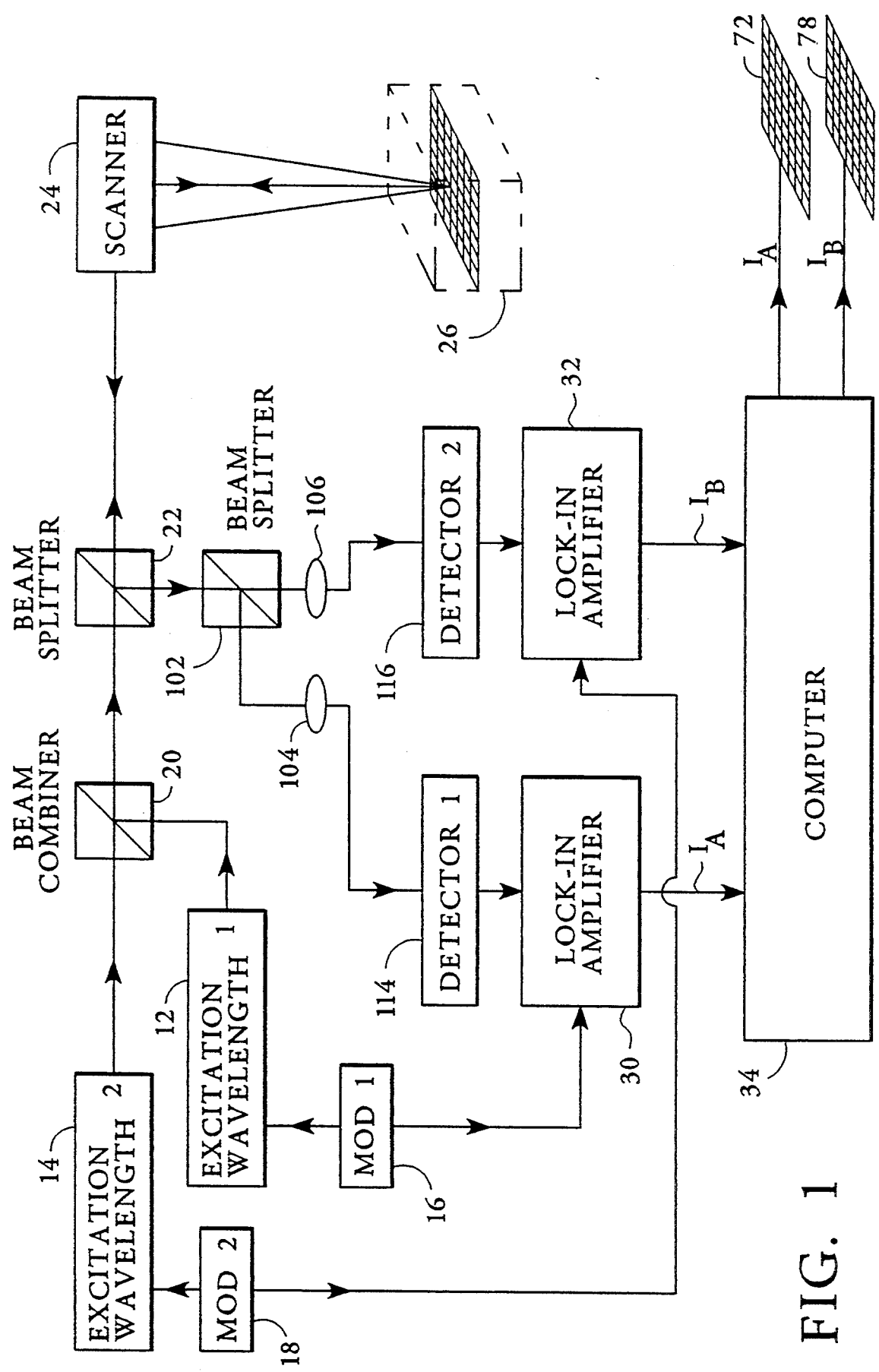
FIG. 1 is a schematic block diagram of a dual detector quantitative microfluorometer in accordance with our invention.

With reference to FIG. 1, a schematic block diagram of a preferred embodiment of the quantitative microfluorometer employing two excitation wavelengths and two lock-in amplifiers is shown. Monochromatic excitation light of different wavelengths is supplied by a pair of light sources 12 and 14. In the preferred embodiment, light sources 12 and 14 are separate diode lasers, although any source of electromagnetic radiation capable of being time-modulated in intensity may be used. The intensity of light source 12 is controlled by a modulator 16 operating at a sinusoidal frequency $\nu_1$. In similar fashion, light source 14 is controlled by a second modulator 18 operating at frequency $\nu_2$. In preferred embodiments, the combination of light source 12 and modulator 16 may alternatively be implemented by a continuous gas laser, followed by an electro-optical or an acousto-optical modulator operating at a frequency $\nu_1$. Likewisely, the combination of light source 14 and modulator 18 may be implemented by a continuous gas laser, followed by an electro-optical or acousto-optical modulator operating at a frequency $\nu_2$. In preferred embodiments, these modulators should be capable of operating at frequencies up to 50 Mhz to cover phase shift measurements according to one of the preferred embodiments. Realistic values of the modulation frequencies in the other embodiments are 2.2 and 3.0 Mhz. Individual light beams from light sources 12 and 14 are combined in a beam combiner 20. The combined beam passes through a beamsplitter 22, which transmits light at the excitation wavelengths $\nu_1$ and $\nu_2$. A scanner 24 sequentially directs the combined beam to locations at sample 26. A realistic value of the sampling frequency of the scanner is 100 khz. In the preferred embodiment, scanner 24 is a confocal laser microscope, although any device capable of focusing excitation at, and collecting emitted radiation from, a discrete location in sample 26 may be used. Sample 26 may be any light-transmitting object containing multiple fluorophores. Such objects include biological cells and two dimensional gels used for separating compounds or dish cultures and the like.

The combined fluorescence emitted in response to excitation at the focal point of scanner 24 is collected by scanner 24 and directed to beamsplitter 22, which has a dichroic element, then passed through another beamsplitter 102, which deflects emitted fluorescence to the two detectors 114 and 116. The semi-reflecting element of the beamsplitter 102 may be a dichroic mirror, performing both beamsplitting and spectral separation. In addition optical filters 104 and 106 may be employed. The effect of the optical filtering performed either by a dichroic element included in beamsplitter 102 or by optical filters 104 and 106, or jointly by these elements, is to separate the collected light into two parts representing different wavelength bands. These parts are distributed to detectors 114 and 116, respectively. Detectors 114 and 116 may be any detectors which produce an electrical signal in response to photons Photomultipliers, which convert photons into electrical signals, are examples of such devices. The signals produced by detectors 114 and 116 are sent to a pair of lock-in amplifiers 30 and 32. Lock-in amplifier 30 is synchronized with the modulation frequency imposed on light source 12 by modulator 16. Similarly, lock-in amplifier 32 is synchronized with the modulation frequency imposed on light source 14 by modulator 18. The phase position of each lock-in amplifier is adjusted to maximize the output.

Referring to FIGS. 4a-d, the curves show the individual spectral components of a combined emission spectrum emitted by two fluorophores in response to excitation by two wavelengths. The curves approximately describe the spectra of two commonly used fluorophores, TRITC (fluorophore A) and Lucifer Yellow (fluorophore B). $\lambda_1$ and $\lambda_2$ are selected by examining the absorption spectra 42 and 44 of fluorophores A and B respectively. $\lambda_1$ is chosen to predominantly excite fluorophore A, while $\lambda_2$ is chosen to predominantly excite fluorophore B. Fluorophore A produces a fluorescent emission spectrum 46 ($I_A$) in response to $\lambda_1$. Fluorophore B produces a fluorescent emission spectrum 50 ($I_B$) in response to $\lambda_2$ and a smaller fluorescent emission spectrum 52 ($I_b$) in response to $\lambda_1$. This latter cross-excited spectrum results from the fact that absorption spectra 42 and 44 overlap at the wavelength $\lambda_1$. The combined emission spectrum, in response to excitation by $\lambda_1$ and $\lambda_2$, is composed of the superimposed spectra 46 ($I_A$), 50 ($I_B$) and 52 ($I_b$), as indicated by FIG. 4d.

The contribution 50 ($I_B$) is the only of the three emissions that is modulated with the frequency $\nu_2$. The wavelength band 62 (b) deflected to detector 116 (detector 2) is chosen so as to encompass the major part of the spectral range of contribution 50 ($I_B$). The measured value of the contribution $I_B$, thus separated from any other contributions to the total emission, is then obtained from the output of lock-in amplifier 32.

The contributions 46 ($I_A$) and 52 ($I_b$) are both modulated with frequency $\nu_1$. The wavelength band 60 (a) deflected to detector 114 (detector 1) is chosen so as to exclude the spectral range of contribution 52 ($I_b$) but to encompass the major part of contribution 46 ($I_A$). The measured value of the contribution $I_A$, thus separated from any other contributions to the total emission, is then obtained as an output from lock-in amplifier 30.

The outputs from lock-in amplifiers 30 and 32 are sent to a computer 34. In the preferred embodiments, computer 34 is a digital computer and the outputs from amplifiers 30 and 32 are digitized, before storage, by conventional analog to digital converters. The inputs representing contributions $I_A$ and $I_B$ at discrete locations in sample 26 are stored in a location specific manner in the computer 34 and can be displayed as digital images on a screen. An image representing fluorophore A or an image representing fluorophore B can be displayed separately. Alternatively, an image representing the two fluorophores can be displayed simultaneously, e.g., using colors to distinguish them from each other. Computer 34 may also derive projection images of a stack of recorded images representing a three dimensional transparent volume, such as a cell, marked by two different fluorophores, and display such projection images in a similar fashion on a screen. In FIG. 1, stored data representing measured values of $I_A$ and $I_B$ are mapped into digital images 72 and 78 for visualization.

Figure 2:
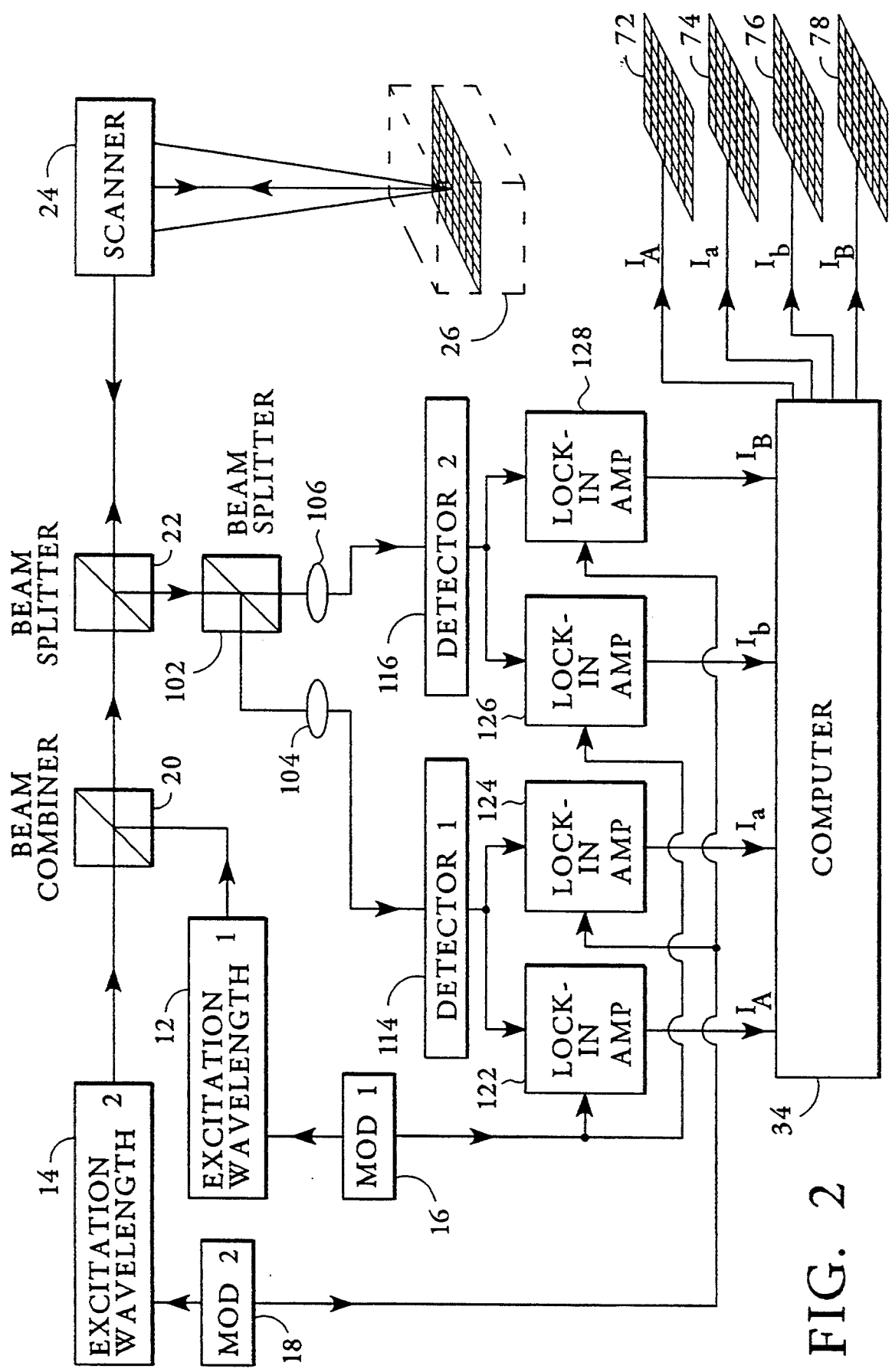
FIG. 2 is a schematic block diagram of a first alternate embodiment of the device of FIG. 1 featuring dual lock-in amplifiers for each detector.

With reference to FIG. 2, two lock-in amplifiers 122 and 124 have been provided for detector 114 (detector 1), and two lock-in amplifiers 126 and 128 for detector 116 (detector 2). Lock-in amplifiers 122 and 26 are locked to modulator 16 (modulator 1), and lock-in amplifiers 124 and 128 to modulator 18 (modulator 2). The phase position of each lock-in amplifier is adjusted to maximize the output.

As before, the wavelength band deflected to detector 116 (detector 2) is chosen so as to encompass the major part of the spectral range of contribution 50 ($I_B$). It will also encompass major parts of the cross-excited contribution 52 ($I_b$). The contribution 50 ($I_B$) is modulated with frequency $\nu_2$, whereas contribution 52 ($I_b$) is modulated with frequency $\nu_1$. Lock-in amplifier 126 is locked to frequency $\nu_1$ and lock-in amplifier 128 to frequency $\nu_2$. The measured value of the contribution 50 ($I_B$) is then obtained as an output from lock-in amplifier 128, separated from any of the other contributions, i.e., separated from contribution 52 ($I_b$) and from contribution 46 ($I_A$), which are both modulated with frequency $\nu_1$. Likewise, the measured value of the contribution 52 ($I_b$) is obtained as an output from lock-in amplifier 126, separated from contribution 50 ($I_B$) which is modulated with the frequency $\nu_2$, and possibly with some interference from contribution 46 ($I_A$), the spectral range of which lies essentially in the wavelength band deflected to detector 114 (detector 1). If this interference is not negligible, it can be compensated for, as will be explained below.

The wavelength band deflected to detector 114 (detector 1) is chosen so as to exclude the spectral range of contribution 52 ($I_b$) but to encompass the major part of contribution 46 ($I_A$), modulated with frequency $\nu_1$. The measured value of the contribution 46 ($I_A$) is obtained as an output from lock-in amplifier 122, which is tuned to frequency $\nu_1$, separated from all other contributions, including contribution 50 ($I_B$), which is modulated with the frequency $\nu_2$.

The measured value of the contribution 46 ($I_A$) does not include the minor part of that contribution which is deflected to detector 116 (detector 2). In cases where this minor part, which by an estimable amount is proportional to the measured part deflected to detector 114 (detector 1), is not negligible, it can be obtained directly as a proportion of the measured part of contribution 46 ($I_A$) obtained from detector 114 (detector 1). Thus, if necessary, measured values from detector 116 (detector 2) can be corrected for the interference from contribution 46 ($I_A$) by subtracting this proportion. This operation is preferably performed by computer 34.

The purpose of lock-in amplifier 124, tuned to frequency $\nu_2$, is to provide an output which is a measured value of a possible contribution $I_a$, representing a cross-excited contribution from fluorophore A excited by wavelength $\nu_2$. This contribution will occur if absorption spectra 42 and 44 overlap also at wavelength $\nu_2$. For simplicity, this is not the case in FIG. 4. The main part of the contribution $I_a$, if occurring, is located within the spectral range 60 (a) passed to detector 114.

In prior application Ser. No. 08/011,881, an alternate method, based on data processing, is described how to derive the contributions $I_A$, $I_a$, $I_b$ and $I_B$. In application Ser. No. 08/011,881, these quantities are denoted $I_{A1}$, $I_{A2}$, $I_{B1}$ and $I_{B2}$, respectively. An underlying assumption in that application is that for each fluorophore, the cross-excited emission is proportional to the main emission. The extension presented by the present application, where optical filtering is added, implies that no such assumption is necessary.

The outputs from lock-in amplifiers 122, 124, 126 and 128 are sent to a computer 34. The inputs to computer 34 representing contributions $I_A$, $I_a$, $I_b$ and $I_B$, respectively, at discrete locations in sample 26 are stored in a location specific manner in the computer 34 and can be displayed as digital images on a screen. As explained in the description of the previous embodiment, they can be displayed separately or in combinations and in projection images from a volume. In addition, quotient images can be presented, representing $I_a/I_A$ or $I_b/I_B$, conveying information about the shape of the excitation spectra of fluorophores A and B, respectively. In FIG. 2, stored data representing measured values of $I_A$, $I_a$, $I_b$ and $I_B$ are mapped into digital images 72, 74, 76 and 78 for visualization.

Figure 3:
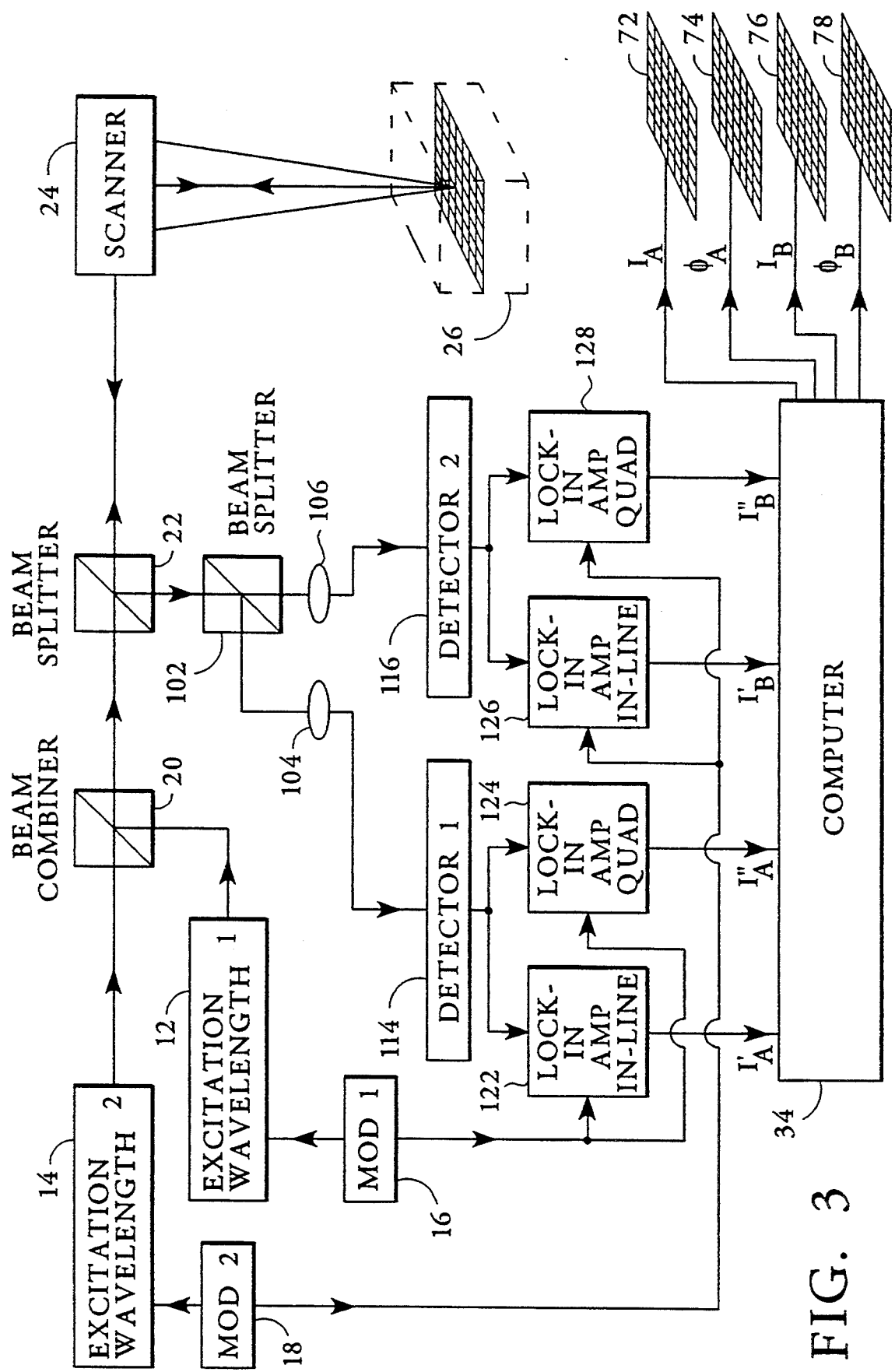
FIG. 3 is a schematic block diagram of a second alternate embodiment of the device of FIG. 1 featuring dual lock-in amplifiers for each detector configured for phase discrimination as well as frequency discrimination.

A variation of the apparatus of FIG. 2 is shown in FIG. 3, where lock-in amplifiers 122 and 124 are both locked to modulator 16, and lock-in amplifiers 126 and 128 are both locked to modulator 18. The phase position of amplifier 124 is shifted 90° relatively to the phase position of amplifier 122 and the phase position of amplifier 128 is shifted 90° relatively to that of amplifier 126. Together, amplifiers 122 and 124 constitute a two-phase lock-in amplifier with an in-line and a quadrature channel. In the same way, amplifiers 126 and 128 also constitute such an amplifier. The outputs I' and I'' of a two-phase lock-in amplifier constitute the x and y components of a vector, which, in polar coordinates, represents the magnitude and the phase angle of the signal applied to the amplifier. The transformation to obtain this magnitude and this phase angle from each two-phase lock-in amplifier is performed by the computer 34.

The phase angle, apart from an off-set that can be eliminated by adjustment of the two-phase lock-in amplifier, represents the phase shift between the waveform of the modulated excitation and the waveform of the detected emission. With modulation frequencies 2.2 and 3.0 Mhz and with fluorophores that are commonly used for labeling, the phase angle shift will be very small, on the order of a few degrees. It will not change substantially from one location of the specimen to another. Therefore, the adjustment of the phase position of a lock-in amplifier to maximize the output is generally quite uncritical. This kind of adjustment has to be performed when using the lock-in amplifiers in the embodiments described earlier. If modulation frequencies are used that are much higher and/or fluorophores are used that have long decay times, substantial phase shifts may appear. This is the case assumed for the present embodiment. From the outputs of amplifiers 122 and 124, the phase shift $\phi_A$ of fluorophore A is derived by the computer 34, and from the outputs of amplifiers 126 and 128, the phase shift $\phi_B$ of fluorophore B is derived by the computer 34.

The magnitude derived by the computer from the outputs of amplifiers 122 and 124 is the measured value of the emission spectrum $I_A$, isolated from other contributions to the total emission in an identical way as described in the specification of the embodiment according to FIG. 1. Analogously, the magnitude derived by the computer from the outputs of amplifiers 126 and 128 is the measured value of the emission spectrum $I_B$. The phase shift $\phi$ of a fluorophore is directly related to the decay time $\tau$ of the fluorophore according to the relationship $\tan \phi = 2\pi \nu \tau$ where $\nu$ is the modulation frequency. From the measured phase shift, the decay time can thus be determined. Thus, decay times for each pixel of a scanned image can be calculated and displayed, supplying, in addition to an intensity image of the fluorophore, also a decay time image, alternatively referred to, in the literature, as a "Fluorescence Lifetime Image". This is performed, simultaneously and independently, for two fluorophores, A and B. In FIG. 3, stored data representing measured values of $I_A$, $\phi_A$, $I_B$ and $\phi_B$ are mapped into digital images 72, 74, 76, 78 for visualization.

We claim:

1. A device for quantifying fluorescent targets, spatially distributed in a plane, by excitation with electromagnetic radiation of multiple discrete wavelengths comprising,
   means for directing dual beams of electromagnetic radiation having different discrete wavelengths at a plurality of individual locations in a scanning manner on a plane where fluorescent targets are present, causing excitation of the targets;
   means for modulating each of said beams at separate modulation frequencies to give each of said beams a specific time modulated waveform;
   means for collecting radiation emitted at locations in said plane in response to said excitation;
   means for optically separating spectral parts of said emitted radiation, said spectral parts representing at least two different wavelength bands;
   means for independently detecting radiation representing each of said separated spectral parts of said emitted radiation;
   demodulation means for extracting from each of said detected spectral parts of the combined emitted radiation from multiple fluorescent targets the contributions corresponding to each of said targets, thereby quantifying each target in said plane.

2. The device of claim 1 wherein each of said beams is produced by a separate diode laser, each of said diode lasers being modulated in intensity with a separate frequency.

3. The device of claim 1 wherein said means for modulating each of said beams comprises an electro-optical modulator for each beam, each of the beams modulated at a separate frequency.

4. The device of claim 1 wherein said means for modulating each of said beams comprises an acousto-optical modulator for each beam, each of the beams modulated at a separate frequency.

5. The device of claim 1 wherein said means for independently detecting spectral parts of said combined emission comprises dual detectors and said means for optically separating spectral parts comprises optical filters arranged to distribute spectrally separated parts of said combined fluorescent emission to each of said dual detectors.

6. The device of claim 5 wherein said demodulation means include separate demodulation means for each of said dual detectors, said demodulation means being specific for signals having the same frequencies as the modulation frequency of a corresponding beam, and the output of each demodulation means being specific to a particular phase position of the modulated waveform.

7. The device of claim 6 wherein said demodulation means includes a single-phase lock-in amplifier for each of the dual detectors, said amplifier being synchronized with the modulation frequency of the corresponding beam.

8. The device of claim 7 wherein the phase position of each of said single-phase amplifiers is tuned to the position which maximizes the output of said amplifier from a corresponding fluorescent target.

9. The device of claim 6 wherein said demodulation means include two single-phase lock-in amplifiers for each of said dual detectors, one being synchronized with the modulation frequency of one of said exciting beams, the other with the modulation frequency of the other, whereby cross-excited spectra are simultaneously and independently measured.

10. The device of claim 6 wherein said demodulation means includes a dual-phase lock-in amplifier for each of said dual detectors, whereby phase shifts of two fluorescent targets are simultaneously and independently measured.

11. The device of claim 1 wherein said means for collecting radiation emitted at locations in said plane is a confocal microscope.

12. A device for quantifying fluorescent targets, spatially distributed in a volume, by excitation with electromagnetic radiation of multiple discrete wavelengths comprising,
    means for directing dual beams of electromagnetic radiation having different discrete wavelengths at a plurality of individual locations in a scanning manner on a scan plane of a volumetric sample, where one or more fluorescent targets are present, causing excitation of the target;
    means for modulating each of said beams at separate modulation frequencies to give each of said beams a specific time-modulated waveform;
    confocal means for collecting radiation emitted at locations in the scan plane in response to said excitation;
    means for optically separating spectral parts of said emitted radiation, said spectral parts representing at least two different wavelength bands;
    means for independently detecting radiation representing each of said separated spectral parts of said emitted radiation;
    demodulation means for extracting from each of said detected spectral parts of the combined emitted radiation from multiple fluorescent targets the contributions corresponding to each of said targets, thereby quantifying each target on the scan plane;
    means for changing the scan plane to another scan plane of the volumetric sample; and
    means for storing data for a plurality of scan planes representing quantification of fluorescent targets in a volumetric sample.

13. The device of claim 12 wherein each of said beams is produced by a separate diode laser, each of said diode lasers being modulated with a separate frequency.

14. The device of claim 12 wherein said means for modulating each of said beams comprises an electro-optical modulator for each beam.

15. The device of claim 12 wherein said means for modulating each of said beams comprises an acousto-optical modulator for each beam.

16. The device of claim 12 wherein said means for independently detecting spectral parts of said combined emission comprises dual detectors and said means for optically separating spectral parts comprises optical filters arranged to distribute spectrally separated parts of said combined fluorescent emission to each of said dual detectors.

17. The device of claim 16 wherein said demodulation means include separate demodulation means for each of said dual detectors, said demodulation means being specific for signals having the same frequencies as the modulation frequency of a corresponding beam, and the output of each demodulation means being specific to a particular phase position of the modulated waveform.

18. The device of claim 17 wherein said demodulation means includes a single-phase lock-in amplifier for each of the dual detectors, said amplifier being synchronized with the modulation frequency of the corresponding beam.

19. The device of claim 18 wherein the phase position of each of said single-phase amplifiers is tuned to the position which maximizes the output of said amplifier from a corresponding fluorescent target.

20. The device of claim 17 wherein said demodulation means include two single-phase lock-in amplifiers for each of said dual detectors, one being synchronized with the modulation frequency of one of said exciting beams, the other with the modulation frequency of the other, whereby cross-excited spectra are simultaneously and independently measured.

21. The device of claim 17 wherein said demodulation means includes a dual-phase lock-in amplifier for each of said dual detectors, whereby phase shifts of two fluorescent targets are simultaneously and independently measured.

* * * * *